United States Patent
Hyland (10) Patent No.: US 10,004,364 B2
(45) Date of Patent: Jun. 26, 2018

(54) DRIP TRAY

(71) Applicant: Kieran Richard Hyland, Blarney (IE)

(72) Inventor: Kieran Richard Hyland, Blarney (IE)

( * ) Notice: Subject to any disclaimer, the term of this patent is extended or adjusted under 35 U.S.C. 154(b) by 0 days. days.

(21) Appl. No.: 14/369,749

(22) PCT Filed: Dec. 31, 2012

(86) PCT No.: PCT/EP2012/077114
§ 371 (c)(1),
(2) Date: Jun. 30, 2014

(87) PCT Pub. No.: WO2013/098417
PCT Pub. Date: Jul. 4, 2013

(65) Prior Publication Data
US 2014/0368320 A1    Dec. 18, 2014

(30) Foreign Application Priority Data

Dec. 30, 2011  (GB) .................................. 1122456.5

(51) Int. Cl.
| | |
|---|---|
| *A47K 5/06* | (2006.01) |
| *A47K 3/00* | (2006.01) |
| *A47K 5/00* | (2006.01) |
| *G08B 21/24* | (2006.01) |
| *G16H 40/20* | (2018.01) |
| *A47K 5/12* | (2006.01) |

(52) U.S. Cl.
CPC ................ *A47K 5/06* (2013.01); *A47K 3/004* (2013.01); *A47K 5/00* (2013.01); *G08B 21/245* (2013.01); *G16H 40/20* (2018.01); *A47K 5/1217* (2013.01); *A47K 2201/02* (2013.01)

(58) Field of Classification Search
CPC ..... G06F 19/327; G08B 21/245; A47K 3/004; A47K 5/00; A47K 5/1217; A47K 2201/00; A47K 2201/02; A47K 5/06
USPC ................ 340/10.4, 12.51, 13.26, 539.12
See application file for complete search history.

(56) References Cited

U.S. PATENT DOCUMENTS

| | | | |
|---|---|---|---|
| 5,793,653 A | 8/1998 | Segal | |
| 5,945,910 A * | 8/1999 | Gorra | G16H 40/20 340/573.1 |
| 7,551,092 B1 * | 6/2009 | Henry | G08B 21/245 340/286.07 |
| 2002/0000449 A1 * | 1/2002 | Armstrong | A47K 5/1217 222/52 |
| 2002/0135486 A1 | 9/2002 | Brohagen et al. | |

(Continued)

*Primary Examiner* — Thomas Alunkal
(74) *Attorney, Agent, or Firm* — Valauskas Corder LLC (57) ABSTRACT

This invention relates to a wall mountable drip tray (1) of the type comprising a mounting plate (5) for mounting the drip tray to a wall, a liquid reservoir (7) extending forwardly from the mounting plate and in which the wall mountable drip tray further comprises monitoring equipment (9) including a proximity sensor (8) for detecting an individual or equipment in the vicinity of the drip tray. The monitoring equipment further comprises a transceiver for communicating with one or more of a remote control unit (23), a fixed network unit (35) and a mobile network unit (37) of a monitoring system (21). By providing such a wall mountable drip tray, existing hand hygiene infrastructure, specifically wall mounted antibacterial liquid dispensers, in an installation can be incorporated into a new monitoring system and will not become obsolete.

20 Claims, 5 Drawing Sheets

(56) References Cited

U.S. PATENT DOCUMENTS

| | | | |
|---|---|---|---|
| 2007/0096930 A1* | 5/2007 | Cardoso | G08B 21/245 340/573.4 |
| 2007/0215239 A1* | 9/2007 | Dorney | A47G 19/2227 141/94 |
| 2007/0257803 A1* | 11/2007 | Munro | G08B 21/245 340/573.1 |
| 2008/0246599 A1* | 10/2008 | Hufton | G01S 1/70 340/529 |
| 2009/0087028 A1 | 4/2009 | Lacey et al. | |
| 2009/0195385 A1* | 8/2009 | Huang | G08B 21/245 340/572.1 |
| 2010/0117836 A1* | 5/2010 | Seyed Momen | G01S 1/70 340/573.1 |
| 2010/0328076 A1* | 12/2010 | Kyle | G06F 19/3418 340/573.1 |
| 2010/0328443 A1 | 12/2010 | Lynam et al. | |
| 2010/0332022 A1* | 12/2010 | Wegelin | G16H 40/20 700/231 |
| 2011/0291841 A1* | 12/2011 | Hollock | G08B 21/245 340/573.1 |
| 2012/0112914 A1* | 5/2012 | Wegelin | A47K 5/1217 340/573.1 |
| 2012/0218106 A1* | 8/2012 | Zaima | A61L 2/26 340/540 |
| 2013/0018506 A1* | 1/2013 | Cittadino | A47K 5/1202 700/240 |
| 2013/0027199 A1* | 1/2013 | Bonner | G08B 21/24 340/539.11 |

* cited by examiner

DRIP TRAY

INTRODUCTION

This invention relates to a drip tray. More specifically, this invention relates to a drip tray particularly suitable for use in one of a system and method for monitoring hygiene standards compliance and a method and system for monitoring the location of a mobile network unit.

Reference is made to the Applicants own granted European Patent No. 1,982,314 entitled "A system and method for monitoring hygiene standards compliance", the Applicants own European Patent Application Publication No. 2,317,700, which is a divisional of European Patent No. 1,982,314 and is also entitled "A system and method for monitoring hygiene standards compliance", and the Applicants own U.S. Pat. No. 8,045,498 entitled "System and method for monitoring the location of a mobile network unit", the entire disclosures of which and in particular the disclosures in relation to the operation and the individual components of the various systems and the individual steps of the tracking methods are incorporated herein by way of reference.

Various systems and methods have been devised to track the location of workers and equipment and to improve hygiene standards compliance in a healthcare facility including those methods and systems described in EP1,982,314, EP2,317,700 and U.S. Pat. No. 8,045,498. These methods and systems have been shown to improve hygiene standards compliance by healthcare workers and other personnel working in healthcare facilities. The improvement of hygiene standards compliance is believed to reduce the likelihood of Hospital Acquired Infections (HAIs) being transmitted to patients in the facility by the staff of the healthcare facility. Furthermore, these systems and methods permit accurate tracking of personnel and equipment which provides improved accountability for personnel's actions in the facility.

There are however some drawbacks with the existing systems and methods. Although very effective in monitoring hygiene standards compliance and encouraging improved hygiene standards, there is reluctance in some quarters to implement the improved methods and systems. This is due to a number of factors. First of all, any existing equipment such as antibacterial gel dispensers already in place in the facility will not form part of the new monitoring system and therefore there is a perception that the capital expenditure on the existing equipment will have been wasted and that existing equipment will be rendered practically redundant (if indeed it is retained) once the new system is installed. This is seen as a waste of financial resources. Furthermore, if the existing equipment is not replaced by equipment that may be monitored closely, the accuracy of the new monitoring method and system will not be entirely reliable as there are devices in the facility that can be used by personnel but that are not part of the new system and method. Therefore, implementation of the new methods and systems can place the operator of the facility in a "Catch 22" type situation which can delay the deployment of the new methods and systems in a facility.

In addition to the above, the known methods and systems, although highly effective in use, may be perceived as relatively limited in their operation and it is advantageous to increase the functionality and usefulness of the existing equipment wherever possible. In this way, a more complete solution may be provided.

It is an object of the present invention to provide a drip tray that helps to overcome at least some of the disadvantages of the known methods and systems.

STATEMENTS OF INVENTION

According to the invention there is provided a drip tray of the type comprising a wall mountable drip tray of the type comprising a mounting plate for mounting the drip tray to a wall, a liquid reservoir extending forwardly from the mounting plate and in which the wall mountable drip tray further comprises monitoring equipment including a proximity sensor for detecting an individual or equipment in the vicinity of the drip tray and a transceiver for communicating with one or more of a remote control unit, a fixed network unit and a mobile network unit of a monitoring system.

By having such a drip tray, the drip tray may be installed beneath an existing wall mounted antibacterial liquid dispenser and used to monitor the usage of the existing wall mounted antibacterial liquid dispenser or detect people or equipment in the vicinity of the drip tray. The results of the monitoring can be used in tracking the location of personnel and or generating a hygiene compliance profile for one or more personnel. This will enable existing equipment in the medical facility to be used in conjunction with the apparatus of the new systems to monitor personnel in the medical facility. In this way, the existing equipment will not have to be discarded but instead may be retained without having a negative impact on the veracity of the new tracking methods and systems.

In one embodiment of the invention the monitoring equipment further comprises a code reader. The code reader may be a bar code reader, a QR code reader or the like.

In one embodiment of the invention the monitoring equipment further comprises a camera or sensor for monitoring hand hygiene performance. The terms hand washing and hand hygiene have been used interchangeably in this specification and it will be understood that both terms will be intended to mean sanitizing the hands with an antibacterial gel or the like material and not simply washing the hands with water. It is envisaged that the hand hygiene liquid or gel may be provided with a tracer that can be detected by the camera in a chosen light spectrum. If the tracer from the liquid or gel is still present after a hand hygiene exercise (or indeed if there is not a sufficient covering of the hands with the gel or liquid before a hand hygiene exercise), this may be indicative of the hand hygiene exercise not being completed adequately. The camera or sensor can therefore detect whether or not the user has correctly washed their hands and alarms or reports may be generated on the strength of the shot taken by the camera.

In one embodiment of the invention the monitoring equipment further comprises a video camera capable of taking a video clip of the individual using a liquid dispenser associated with the drip tray. By taking a video clip of the individual using the liquid dispenser, the device can provide proof that a given individual was in the vicinity of the dispenser and in some instances whether or not they used the dispenser. The video camera and indeed other cameras may also be capable of capturing other actions such as recording visits to a patient and or certain actions performed in association with certain patients in the vicinity of the drip tray. For example, it is envisaged that a video clip may be captured of an elderly patient being fed or being visited a predetermined number of times over a given period of time. This may be particularly important for elderly patients suffering from dementia or like illness to ensure that they are receiving an adequate standard of care.

In one embodiment of the invention the drip tray is provided with means to monitor a liquid dispenser with which it is associated. It is envisaged that the drip tray can monitor the properties of the liquid dispenser including, but not limited to, when and/or whether or not the liquid dispenser is operated and the amount of liquid still in the liquid dispenser. It is envisaged that the drip tray, when monitoring the amount of antibacterial liquid in the liquid dispenser, can also be used to notify an operator if the liquid in the dispenser needs to be topped up. In this way, an alert may be transmitted to the operator or to an individual responsible for maintaining the dispenser. In order to do so, a sensor may need to be placed in the dispenser itself (unless already provided) and would be in wired or wireless communication with the monitoring equipment in the drip tray. The sensor could detect the amount of antibacterial liquid in the liquid dispenser and an alert could be generated on the antibacterial liquid running low and or running out.

In one embodiment of the invention the monitoring equipment further comprises a sensor to detect an identification device carried by a user in the vicinity of the drip tray. In one embodiment of the invention the sensor comprises an RFID reader. This is seen as a particularly preferred aspect of the invention. By detecting an identification device, such as, but not limited to, an RFID tag worn by personnel, the information can be used in a system and method for monitoring the location of and or the hygiene standards compliance of the personnel.

In one embodiment of the invention the proximity sensor comprises a PIR sensor. This is seen as a simple sensor to use and can be used to turn the device on for a given period of time once the sensor detects a person in the proximity of the tray. This will allow for power conservation thereby reducing the maintenance requirement of the drip tray.

In one embodiment of the invention the monitoring equipment further comprises an identification verification module mounted on the drip tray.

In one embodiment of the invention the wall mountable drip tray is a fixed network unit of a monitoring system. This is seen as a particularly preferred embodiment of the present invention. It is envisaged that the drip tray can operate as a fixed node of a mesh network, such as, but not limited to, a ZigBee (Registered Trade Mark®) network or like low powered wireless network. Data from that drip tray and other fixed nodes can be routed through the drip tray to a control unit to facilitate monitoring of individuals associated with the facility.

In one embodiment of the invention the mounting plate is releasably detachable from the body.

In one embodiment of the invention the mounting plate comprises at least one mounting point for reception of a fixing member to secure the mounting plate to a wall.

In one embodiment of the invention the drip tray liquid reservoir will be removable from the drip tray. This will facilitate cleaning of the liquid reservoir.

In one embodiment of the invention there is provided a hygiene monitoring system for monitoring hygiene standards compliance by individuals in a facility, the system comprising a surveillance network having a control unit and a plurality of mobile network units, each of the mobile network units having a transmitter for transmitting an identification signal particular to an individual associated with that mobile network unit to the control unit, the surveillance network further comprising a plurality of fixed network units dispersed throughout the facility, each of the fixed network units having a transceiver to receive identification signals from the mobile network units and transmit the identification signals onward to the control unit, the mobile network units and the fixed network units form part of a wireless personal area network (WPAN), the control unit further comprising a processor, an accessible memory and a receiver for receiving the identification signals from the mobile network units, the control unit storing the identification signals in accessible memory and the processor having means to analyse the identification signals in accessible memory and generate a hygiene standards compliance profile for the individual associated with that mobile network unit, and in which at least one of the fixed network units forms part of a wall mountable drip tray according to the present invention.

In one embodiment of the invention there is provided a method of monitoring hygiene standards compliance by individuals in a facility, the facility having a surveillance network comprising a control unit and a plurality of mobile network units, each of the mobile network units having a transmitter for transmitting an identification signal particular to an individual associated with the mobile network unit to the control unit, the surveillance network further comprising a plurality of fixed network units dispersed throughout the facility, each of the fixed network units having a transceiver to receive identification signals from the mobile network units and transmit the identification signals onward to the control unit, the mobile network units and the fixed network units form part of a wireless personal area network (WPAN), the monitoring unit having a processor, an accessible memory and a receiver for receiving identification signals, the method comprising the steps of: the mobile network units transmitting identification signals particular to the individual associated with the mobile network unit to the control unit via at least one of the fixed network units in the WPAN; the control unit storing the identification signals in accessible memory; the control unit analysing the identification signals stored in accessible memory and thereafter generating a hygiene standards compliance profile for one or more of the individuals associated with the mobile network units; and in which at least one of the fixed network units forms part of a wall mountable drip tray according to the present invention.

DETAILED DESCRIPTION OF THE INVENTION

The invention will now be more clearly understood from the following description of some embodiments thereof given by way of example only with reference to the accompanying drawings, in which:—

Figure 8:
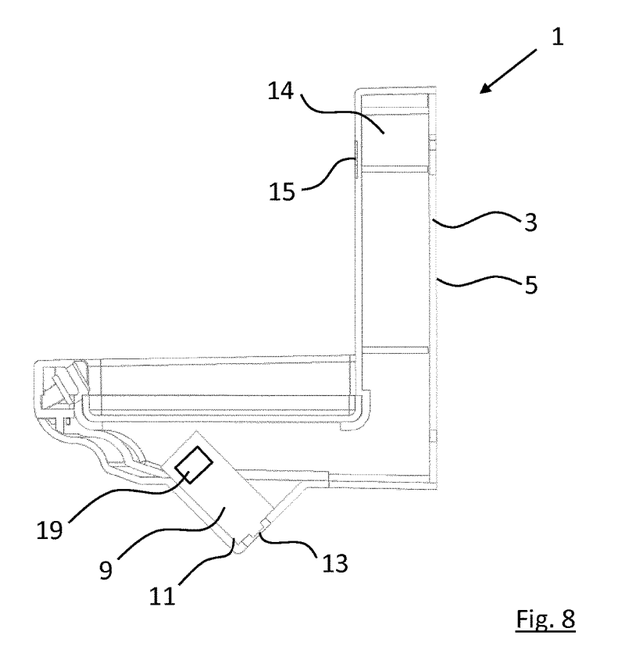
FIG. 8 is a cross sectional view along the lines I-I of the drip tray of FIG. 2.

Referring to FIGS. 1 to 8, there is shown a drip tray, indicated generally by the reference numeral 1, comprising a body 3 having a mounting plate 5 and a liquid reservoir 7 for collection of drips from an antibacterial fluid dispenser (not shown) mounted above the drip tray when in use. The drip tray comprises a proximity sensor, in this case a passive infrared sensor (PIR) sensor 8 mounted on the front of the body to detect an individual approaching the drip tray. The PIR sensor, on detecting the presence of an individual, wakes up the remaining equipment and electronics 9 mounted internal the drip tray (FIG. 8).

The drip tray further comprises a code reader 11, in this case the code reader is provided by a combined bar code and QR code reader however other code readers are also envisaged. The code reader has a screen 13 with scanning equipment (not shown) located behind the screen 13. The scanning equipment is standard scanning equipment commonly used in the art to scan bar codes and QR codes and further description of the scanning apparatus is deemed unnecessary. The code reader is directed towards the rear of the drip tray however it could be angled towards the front of the drip tray if preferred. The drip tray 1 further comprises a camera 14 behind a protective screen 15 for taking one or both of a still shot and a video clip. One or more cameras may be provided behind the screen 15 for capturing various photographic images or video images.

For example, a camera may be provided for monitoring the effectiveness of hand washing by personnel. This is achieved by providing a camera that operates in a light spectrum (e.g. Ultraviolet (UV)) that picks up a dye in an antibacterial liquid used in a dispenser associated with the drip tray. The UV camera can capture images of the operators hands prior to, during and/or after a hand washing exercise and those images can be processed by a local or a remote processor (not shown) to determine whether or not the hand washing exercise has been successful. If all of the dye is washed away after a hand washing exercise, this is indicative that the hand washing has been completed successfully and the UV camera and processor may be used in this manner to monitor the hand washing effectiveness of an individual. Similarly, the UV camera and processor may be used to check that there is an adequate covering of the hands with the antibacterial fluid prior to washing or that there is an adequate covering of the hands with the antibacterial liquid if it is the type that does not require subsequent washing with water. The UV camera and the processor may be used together to trigger an alarm if there is still antibacterial fluid present after a hand washing exercise or alternatively if there is an insufficient covering of antibacterial fluid on the hands.

In addition to the UV camera described above, a video camera may be provided to take a video clip of the personnel to provide evidence that they were in the vicinity of the drip tray. Similarly, a camera capable of capturing a still image of the individual may be used if preferred. The video and or the still image can be time stamped to provide more evidence regarding the time and date that the personnel were in the vicinity of the drip tray. If preferred, one or more of the cameras could be located elsewhere on the drip tray, such as, but not limited to, adjacent the liquid reservoir.

The electronics 9 contained in the drip tray comprise a transceiver (not shown) for relaying data in a wireless communication network. The wireless communication network may be, but is not limited to, a WPAN. The WPAN could, for example, be a ZigBee WPAN. The wireless communication network will typically comprise a control unit, a plurality of fixed network units dispersed throughout the facility and one or more mobile network units. The mobile network units communicate with the fixed network units and the fixed network units send information relating to the mobile communications units such as a unique identifier of the mobile network unit and the strength of a signal received from the mobile network unit by the fixed network unit to the control unit. This information can be used to track the whereabouts and the actions of the mobile network units. The fixed network units also relay information received from other fixed network units onwards to the control unit. In this way, the drip tray can perform the functions of a fixed network unit of a monitoring system such as that described in EP1,982,314 or U.S. Pat. No. 8,045,498. The drip tray may be used to relay messages and information relating to mobile network units in the facility to a control unit. The information relating to the mobile network units may have been received directly from the mobile network unit in the vicinity of the fixed network unit or may be received indirectly from another fixed network unit. Preferably, the electronics will comprise an RFID tag reader 19 or other identification tag reader to detect the presence of a mobile network unit having the RFID tag or other identification tag in the vicinity of the drip tray. A power supply (not shown) will also be provided. It is envisaged that the electronics may comprise some memory for storage of data obtained by the sensors to allow subsequent interrogation of the data or subsequent transmission of the data to a control unit.

In the embodiment described, the PIR sensor wakes up the remaining electronics 9 in the drip tray however it will be understood that some or all of the remaining electronics may be on or in a mode capable of receiving signals constantly or for a significant period of time not dependent on the PIR sensor. For example, if the electronics in the drip tray include and operate as a fixed network unit in a monitoring system or wireless communication network such as that described in EP1,982,314 or U.S. Pat. No. 8,045,498, it may be necessary to keep some or all of the electronics on permanently or at other times to ensure that the drip tray can send or receive signals from one or more of mobile network units, a control unit and a plurality of fixed network units dispersed throughout the facility in which the drip tray is installed.

The code reader 11 is seen as a particularly useful addition to the drip tray as the drip tray can be used to scan codes on equipment such as, but not limited to, surgical gowns, surgical gloves, syringes, towels, files and the like or other items such as medicaments, labels or other packaging of equipment that is being used by healthcare personnel. In this way, an inventory of equipment used or medicaments dispensed by the personnel can be taken. Furthermore, a record of the equipment or medicaments used in conjunction with a particular patient may be recorded and stored in memory of a remote control unit. All that is required is for the Health Care Worker (HCW) to present the bar code or the QR code associated with the equipment or medicament to the code reader prior to, during or after using the equipment or medicament and the code reader will register that the equipment or medicament has been used in a particular location, for example a patient's room. Similarly, information concerning the HCW or a piece of equipment, taken for example through interrogation of an RFID tag worn by the user or carried by a piece of equipment, may also be taken to associate use of the equipment with that particular healthcare worker and/or a patient.

Figure 1:
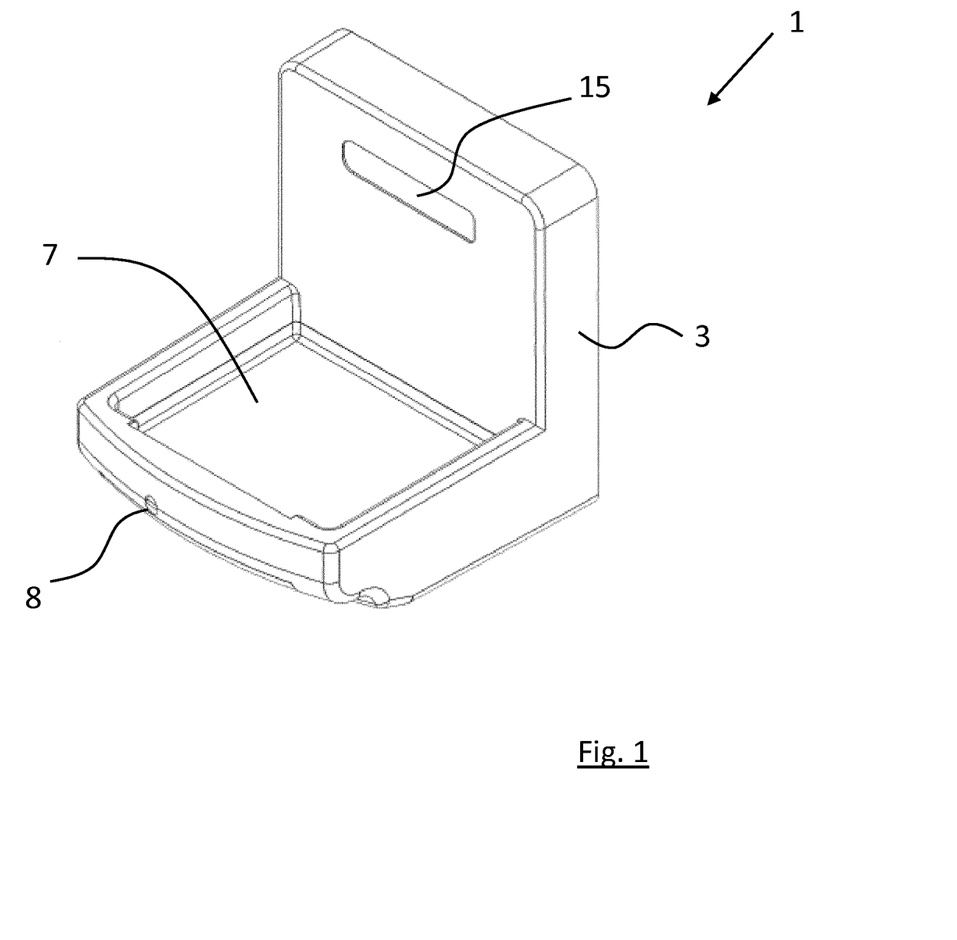
FIG. 1 is an isometric view of a drip tray according to the invention.
Figure 2:
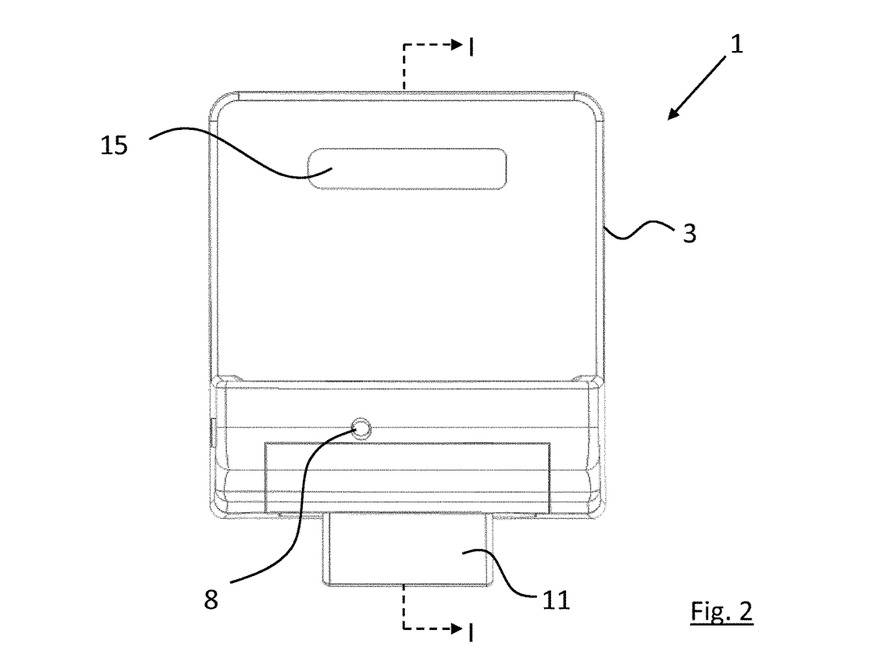
FIG. 2 is a front view of the drip tray of FIG. 1.
Figure 3:
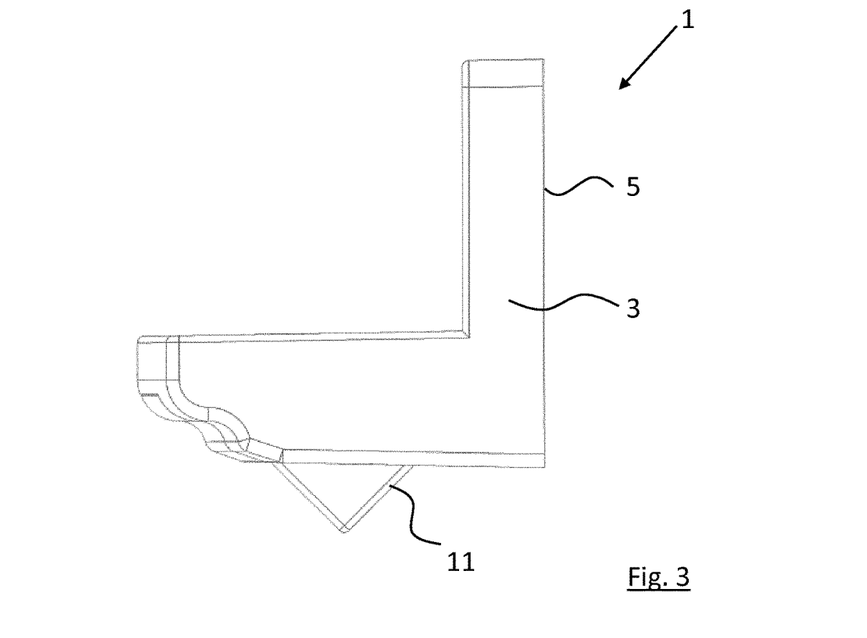
FIG. 3 is a right side view of the drip tray of FIG. 1.
Figure 4:
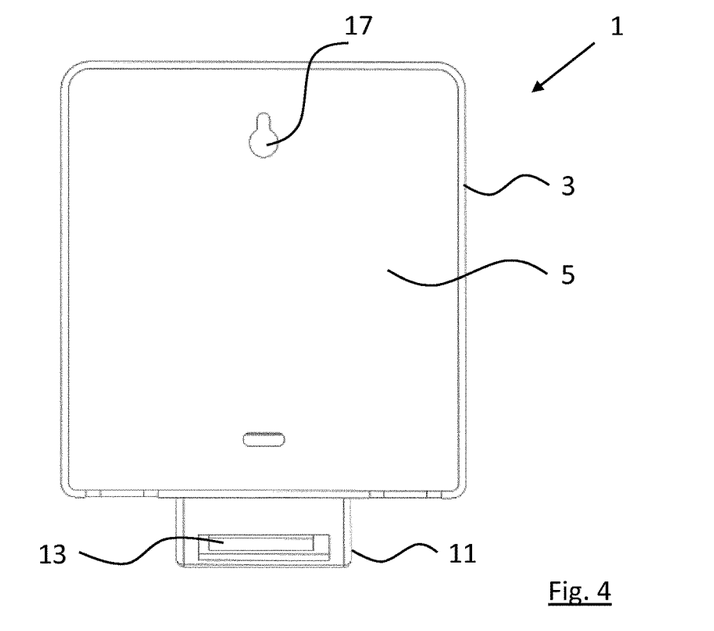
FIG. 4 is a rear view of the drip tray of FIG. 1.
Figure 5:
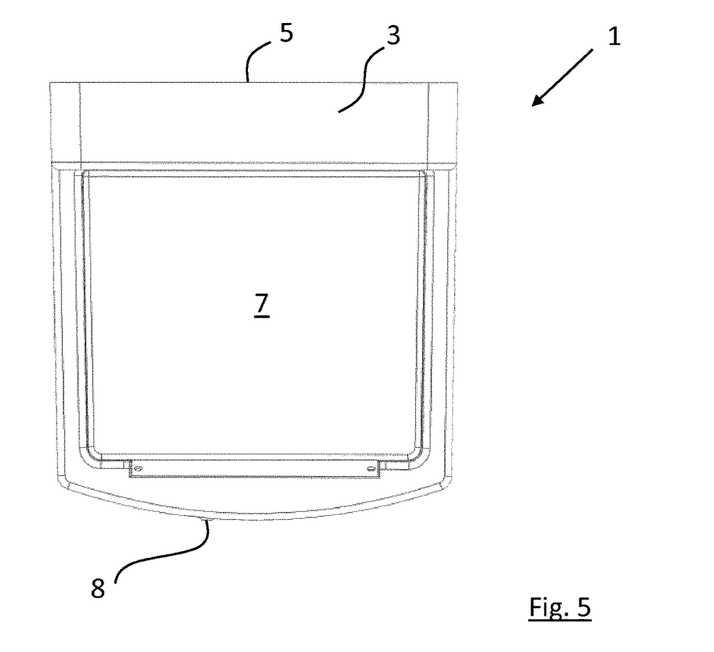
FIG. 5 is a top plan view of the drip tray of FIG. 1.
Figure 6:
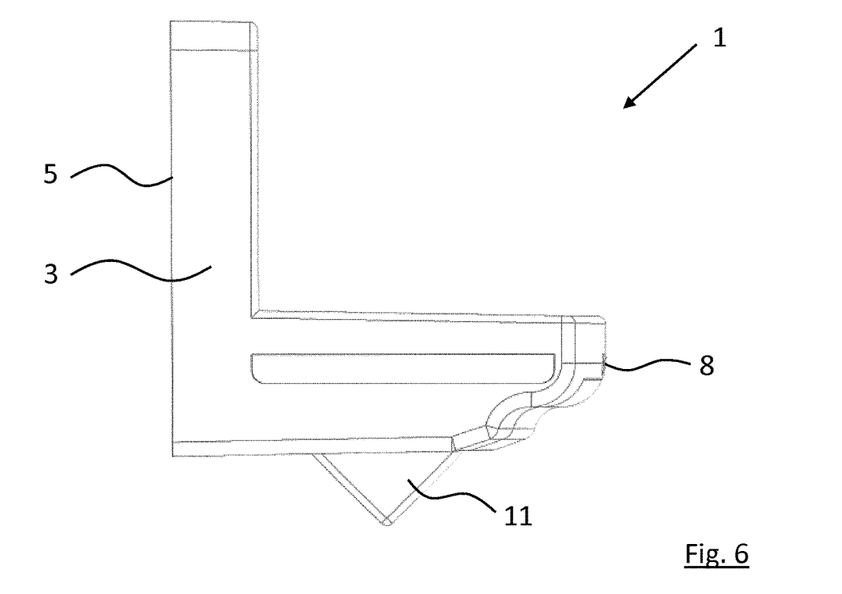
FIG. 6 is a left side view of the drip tray of FIG. 1.
Figure 7:
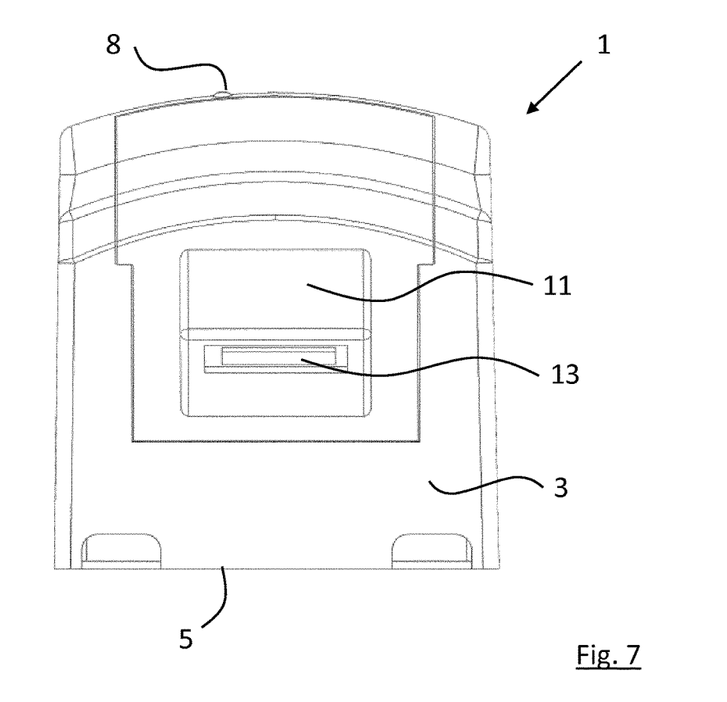
FIG. 7 is a bottom plan view of the drip tray of FIG. 1.

Referring to FIG. 4, there is shown a rear view of the drip tray. The drip tray comprises a mounting plate 5 which is optionally releasably detachable from the remainder of the drip tray body to allow the drip tray to be secured to a wall. A mounting point 17 is provided to receive a fixing member such as a screw to secure the drip tray to the wall.

In addition to the embodiment described, it is envisaged that various other modifications could be made to the drip tray without departing from the spirit of the invention. For example, additional proximity sensors such as a PIR sensor could be placed elsewhere on the drip tray. For example, a proximity sensor could be positioned specifically to detect when an operators hands are above the drip tray in a position to receive liquid from the liquid dispenser to record a liquid dispensing operation. Furthermore, other cameras and/or sensors could be provided adjacent to the code reader beneath the drip tray to validate hand hygiene procedures. Various types of sensors, not only optical sensors, can be used to detect the presence of antibacterial fluid or indeed pathogens or bacteria on the operators hands.

The drip tray according to the invention is a retro-fit unit for all types of wall mounted dispensers without a drip tray or as a substitute drip tray for many types of wall mounted dispensers. The drip tray is suitable for use with a wall mounted dispenser provided by practically any supplier. The drip tray incorporates all the current features and benefits of the fixed network units described in the Applicants granted European Patent EP1,982,314.

Figure 9:
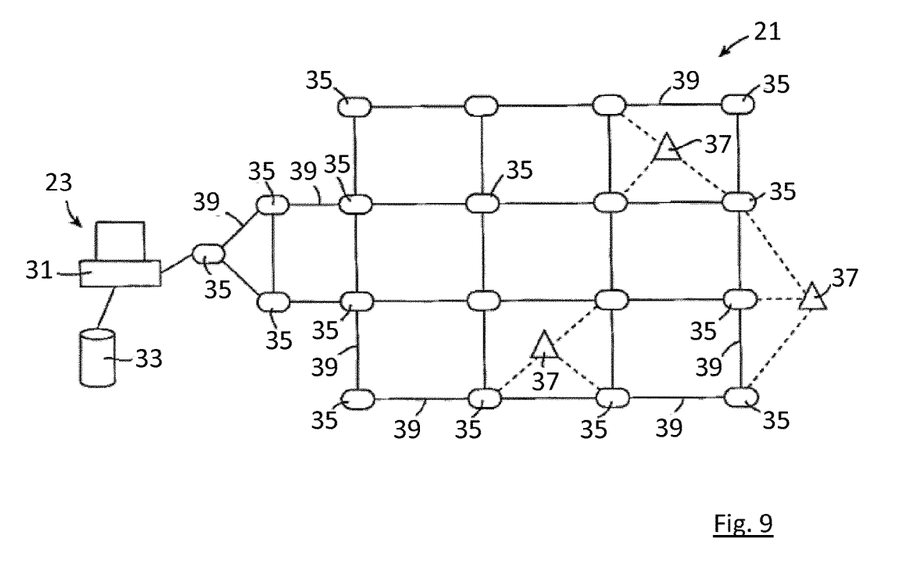
FIG. 9 is a diagrammatic representation of a system in which the drip tray according to the invention may be used.

Referring to FIG. 9, there is shown a diagrammatical representation of a system in which the drip tray according to the invention may be used, indicated generally by the reference numeral 21, comprising a control unit 23, a plurality of fixed network units 35 and a plurality of mobile network units 37. The control unit 23, also referred to as a monitoring unit, the plurality of fixed network units 35 and the plurality of mobile network units 37 are connected by way of a wireless communication network, whose links 39 provide a communications channel from the mobile network units 37 to the monitoring unit 23 via the fixed network units 35. The control unit 23 further comprises a processor 31 and accessible memory 33. Each of the mobile network units comprises a transmitter (not shown) for transmitting an identification signal from the mobile network unit and each of the fixed units comprises a transceiver (not shown) for receiving the identification signals and transmitting the identification signals over the communication links 39 to the control unit 23. The drip trays 1 of the present invention may be used as the fixed network units 35.

In use, a staff member carries a mobile network unit on their parson. This mobile network unit may or may not be formed as part of another device such as an antibacterial fluid dispenser. The mobile network unit 37 periodically transmits an identification signal to the surrounding environment. This identification signal is picked up by any fixed network unit 35 within a predetermined radius, in this case 5 meters, of the mobile network unit. On receipt of the identification signal, the fixed network units that received the identification signal transmit that signal from the fixed network unit 35 to the control unit 23 where the processor 31 determines the identity of the transmitting mobile communication unit and thereafter logs the information in memory 33 for subsequent analysis.

The information sent by the fixed network units 35, including one or more drip trays 1, further comprises signal strength data and when the processor 31 receives the signal strength data along with the identification data, the processor may determine the location of the mobile network unit 37. Therefore, the position of the mobile network unit 37 at that moment in time may be determined. In addition to periodically transmitting the identification signal, the mobile monitoring unit also transmits data in response to the actions of the user carrying the mobile network unit. For example, if the mobile network unit forms part of an antibacterial fluid dispenser used for washing the member of staff's hands, the mobile network unit may be arranged to transmit a definitive identification signal an the actuation of the dispensing mechanism indicating that the employee has washed their hands with antibacterial fluid in accordance with best practice in the control of infectious diseases in a hospital environment. This act will be logged as a hand washing incident in the control unit memory 33 along with the identification signal data indicating the particular employee and their location at that time, Similarly, the users action that causes the transmission of an identification signal may be the user moving within a certain distance of a drip tray in a ward or by operating the antibacterial liquid dispenser associated with the drip tray and these actions will cause the identification signal to be transmitted. When actuated or when moving within a certain distance of the drip tray, the drip tray sends out an identification request which is received by an employee's mobile network unit which responds with its identifier signal. In this instance, the mobile network unit will also be provided by a suitable transceiver or a receiver to receive such signals from the fixed network unit.

The identification signal transmitted by the mobile network unit is transmitted and received by a plurality of fixed network units, in the embodiment shown, three fixed network units 35, one or more of which could be a drip tray according to the present invention, receive the identification signal. In this way, the position of the mobile network unit 37 may be quickly calculated/triangulated on the control unit processor 31 in a simple and efficient manner with the minimum of difficulty. All of the data is then logged by the control unit which may subsequently generate reports based on the mobile network unit's position and usage patterns gleaned from the identification data and accordingly the staff hygiene practices may be carefully monitored. Again, the implementation of such a system is described in detail in the Applicant's own granted European Patent No. EP1,982,314 and the Applicant's own U.S. Pat. No. 8,045,498.

Also included in the drip tray is a multi-type code reader (QR, bar line and the like) for scanning codes on equipment such as disposable gowns, gloves, face masks and other staff and patient protection items. This provides accountability for usage of equipment in the medical facility. In other words, who used the equipment, where did they use it and whom (which patient) was the equipment used in conjunction with. Accountability for syringe, dressings, liquids, medication used on a patient or in and around a patient environment by a Health Care Worker (HCW) or a hygiene operator can be monitored which in conjunction with the HCWs personal hand hygiene unit (as described in detail in EP1,982,314), ID card or tracking tag gives total accountability for the actions and the whereabouts of a HCW in the facility.

The drip tray, the ID card, the personal hand hygiene unit and the tracking tag are all suitable for use in a monitoring system and method that operate using one or more of a WPAN/PAN, a Body Area Network (BAN), ZigBee®, RFID, IR, Ultra Wide Band and Real Time Location System (RTLS) communication networks and location tracking technologies that use these methodologies. Similarly, the devices could be used with other communication networks and tracking technologies. The drip tray may also include one or more of biometric, optical retina and voice scan technologies to identify users of the drip tray and facilitate greater accountability of personnel's actions in the healthcare facility.

Some of the communications in the system could be via GSM communications or the like and it is envisaged that there will be two way communications between the drip tray and other devices including, but not limited to dispensers, machines, personal devices. The personal devices worn by HCWs may be smartphones and communication between the smartphones and the drip tray is readily envisaged. The devices may be equipped for one or more of near field communications (NFC), low frequency (LF) communications and radio frequency (RF) communications if desired.

The HCW is now to a certain extent accountable for clocking a patient in and out for treatment. This will enable charging the patient on a time basis for their treatment or indeed the information may be used for workflow improvement by the healthcare facility management. The patient may be given an identification tag that they carry with them into a treatment room and the drip tray will identify the patient as being in the room. The HCW, when entering the room with the patient, will also scan the bar code (or other code or a tag) associated with that patients file using the code reader (and/or other electronic equipment) of the drip tray. This will verify the location of the patient in the treatment room, the use of that patients file in conjunction with that patient, the duration of time that the patient is in the treatment room, who is providing the patient with treatment and how long the treatment lasts for. Using other aspects of the invention and the monitoring system generally, it will also be possible to determine the equipment used in the treatment of the patient and who used that equipment.

The PIR unit or similar type of switching unit on the drip tray is used to detect a user's hand movement which turns the other electronic equipment of the drip tray on so that the other equipment can detect the user of the liquid dispenser and whether they are a HCW, a Hygiene Operator, an Operator, a Visitor, a patient or the like. An image and scanning lens is incorporated in the unit to scan QR codes and to scan a variety of items including hands, documents, labels, liquid types, medical equipment, medicaments and the like. Food on a food tray may be detected if the food tray or food receptacle is provided with a code or tag that may be detected by the drip tray code reader or tag reader to monitor food provided to patients. Also a video camera may be supplied to provide a live feed or recorded footage of tasks, such as, but not limited to, the feeding of a patient. The live feed or footage can be transferred to a control unit along with information relating to the location of the person or object wearing the location tracking unit.

In this specification the terms "comprise, comprises, comprised and comprising" and the terms "include, includes, included and including" are all deemed totally interchangeable and should be afforded the widest possible interpretation.

The invention is in no way limited by the embodiments hereinbefore described but may be varied in both construction and detail within the scope of the claims.

The invention claimed is:

1. A wall mountable drip tray for installation beneath a pre-existing wall mounted antibacterial liquid dispenser, the wall mountable drip tray being, in use, physically separate and distinct from the pre-existing wall mounted antibacterial liquid dispenser and being of the type comprising a mounting plate for mounting the drip tray to a wall, a liquid reservoir extending forwardly from the mounting plate for collection of drips from the antibacterial fluid dispenser and in which the wall mountable drip tray further comprises monitoring equipment including a proximity sensor for detecting an individual or equipment in the vicinity of the drip tray and a transceiver for communicating with a mobile network unit of a monitoring system and at least one remote control unit and a fixed network unit.

2. The wall mountable drip tray as claimed in claim 1 in which the monitoring equipment further comprises a code reader.

3. The wall mountable drip tray as claimed in claim 1 in which the monitoring equipment further comprises a camera for monitoring hand washing performance.

4. The wall mountable drip tray as claimed in claim 1 in which the monitoring equipment further comprises a video camera capable of taking a video clip of the individual using a liquid dispenser associated with the drip tray.

5. The wall mountable drip tray as claimed in claim 1 in which the wall mounted unit is provided with means to monitor a liquid dispenser with which it is associated.

6. The wall mountable drip tray as claimed in claim 1 in which the monitoring equipment further comprises a sensor to detect an identification device carried by a user in the vicinity of the drip tray.

7. The wall mountable drip tray as claimed in claim 6 in which the sensor comprises an RFID reader.

8. The wall mountable drip tray as claimed in claim 1 in which the proximity sensor comprises a PIR sensor.

9. The wall mountable drip tray as claimed in claim 1 in which the monitoring equipment further comprises an identification verification module mounted on the drip tray.

10. The wall mountable drip tray as claimed in claim 1 in which the wall mountable drip tray is a fixed network unit of a monitoring system.

11. The wall mountable drip tray as claimed in claim 1 in which the mounting plate is releasably detachable from the body.

12. The wall mountable drip tray as claimed in claim 1 in which the mounting plate comprises at least one mounting point for reception of a fixing member to secure the mounting plate to a wall.

13. A wall mountable drip tray for installation beneath a pre-existing wall mounted antibacterial liquid dispenser, the wall mountable drip tray being, in use, physically separate and distinct from the pre-existing wall mounted antibacterial liquid dispenser and being of the type comprising a mounting plate for mounting the drip tray to a wall, a liquid reservoir extending forwardly from the mounting plate for collection of drips from the antibacterial fluid dispenser and in which the wall mountable drip tray further comprises monitoring equipment including means to monitor a liquid dispenser with which it is associated, a proximity sensor for detecting an individual or equipment in the vicinity of the drip tray and a transceiver for communicating with a mobile network unit of a monitoring system and at least one remote control unit and a fixed network unit.

14. The wall mountable drip tray as claimed in claim 13 in which the monitoring equipment further comprises a sensor to detect an identification device carried by a user in the vicinity of the drip tray.

15. The wall mountable drip tray as claimed in claim 14 in which the sensor comprises an RFID reader.

16. The wall mountable drip tray as claimed in claim 13 in which the monitoring equipment further comprises a camera for monitoring hand washing performance.

17. A wall mountable drip tray for installation beneath a pre-existing wall mounted antibacterial liquid dispenser, the wall mountable drip tray being, in use, physically separate and distinct from the pre-existing wall mounted antibacterial liquid dispenser and being of the type comprising a mounting plate for mounting the drip tray to a wall, a liquid reservoir extending forwardly from the mounting plate for collection of drips from the antibacterial fluid dispenser and in which the wall mountable drip tray further comprises monitoring equipment including a proximity sensor for detecting an individual or equipment in the vicinity of the drip tray, a sensor to detect an identification device carried by a user in the vicinity of the drip tray, and a transceiver for communicating with a mobile network unit of a monitoring system and at least one remote control unit and a fixed network unit.

18. The wall mountable drip tray as claimed in claim 17 in which the sensor comprises an RFID reader.

19. The wall mountable drip tray as claimed in claim 17 in which the proximity sensor comprises a PIR sensor.

20. The wall mountable drip tray as claimed in claim 17 in which the monitoring equipment further comprises a video camera capable of taking a video clip of the individual using a liquid dispenser associated with the drip tray.

* * * * *